United States Patent [19]

Manz

[11] Patent Number: 5,392,639

[45] Date of Patent: Feb. 28, 1995

[54] APPARATUS AND METHOD FOR IDENTIFYING AND DISTINGUISHING DIFFERENT REFRIGERANTS

[75] Inventor: Kenneth W. Manz, Paulding, Ohio

[73] Assignee: SPX Corporation, Muskegon, Mich.

[21] Appl. No.: 77,279

[22] Filed: Jun. 17, 1993

[51] Int. Cl.$^6$ .................. F25B 45/00; G01N 29/18
[52] U.S. Cl. .................. 73/61.76; 73/25.04; 422/83; 422/98; 62/476; 62/467
[58] Field of Search .................. 73/61.76, 25.04, 25.01; 422/83, 98; 62/476, 467

[56] References Cited

U.S. PATENT DOCUMENTS

| | | | |
|---|---|---|---|
| 3,264,862 | 8/1966 | Felton et al. | 73/25.01 |
| 3,535,915 | 10/1970 | Felton et al. | 73/25.01 |
| 4,768,347 | 9/1988 | Manz et al. | 62/149 |
| 4,805,416 | 2/1989 | Manz et al. | 62/292 |
| 4,878,356 | 11/1989 | Punches et al. | 62/149 |
| 4,879,546 | 11/1989 | Dunham et al. | 73/24 |
| 4,939,905 | 7/1990 | Manz | 62/77 |
| 5,158,747 | 10/1992 | Manz et al. | 422/98 |
| 5,237,873 | 8/1993 | Eichenlaub | 73/597 |

Primary Examiner—Hezron E. Williams
Assistant Examiner—J. David Wiggins
Attorney, Agent, or Firm—Barnes, Kisselle, Raisch, Choate, Whittemore & Hulbert

[57] ABSTRACT

Refrigerant type is identified and determined by storing in electronic memory indicia representative of saturation pressure/temperature characteristics of a plurality of differing refrigerant types. A liquid refrigerant sample of unknown type is obtained and vaporized under controlled conditions of temperature and pressure. Refrigerant vapor temperature is measured at two different vapor pressures during the vaporization process, and such temperatures and pressures are then compared with the indicia prestored in memory. Two temperature readings at differing vapor pressures are sufficient to distinguish refrigerant type based upon the prestored saturation/temperature indicia.

23 Claims, 3 Drawing Sheets

APPARATUS AND METHOD FOR IDENTIFYING AND DISTINGUISHING DIFFERENT REFRIGERANTS

The present invention is directed to refrigerant handling systems such as air conditioners and heat pumps, and more particularly to an apparatus and method for identifying and distinguishing between different types of refrigerants for service of such systems.

BACKGROUND AND OBJECTS OF THE INVENTION

It is now widely recognized and accepted that release into the atmosphere of chlorofluorocarbon(CFC)-based refrigerants, such as refrigerant R12, has a deleterious effect upon the ozone layer that surrounds the earth. Production of CFC-based refrigerants may be severely curtailed in the future, and the cost of refrigerant for service purposes is already increasing. It is therefore becoming standard practice in the refrigerant system service industry to recover, purify and reuse refrigerant in a refrigeration system under service, rather than merely to vent such refrigerant into the atmosphere and replace with new refrigerant, as had been common practice in the past U.S. Pat. Nos. 4,768,347, 4,805,416 and 4,878,356, all assigned to the assignee hereof, disclose equipment for recovering, purifying and/or recharging refrigerant in a refrigeration system service environment.

As currently envisioned, R12 refrigerant will eventually be replaced by different types of refrigerants in production of new refrigeration systems. For example, R12 refrigerant may be replaced by R134a refrigerant in the automotive industry—i.e., in automotive air conditioning systems. However, because these refrigerants and their associated lubricants-are chemically incompatible with each other, inadvertent mixture of even small amounts of the different refrigerants can cause severe damage and early failure of the refrigeration system. It has been proposed to provide different service fittings on refrigeration equipment using different types of refrigerants, but the use of adaptors and the like in the service industry may still result in inadvertent mixing of refrigerant/lubricant types, with consequent damage to the system under service or to the service equipment itself.

A further complication arises with the use of intermediate refrigerants as substitutes for R12 refrigerant, such as ternary blends made by DuPont. With severe curtailment of R12 production that may take place, it is anticipated that a significant number of refrigeration systems currently employing R12 refrigerant may eventually be retrofitted with an intermediate substitute refrigerant. Inadvertent mixing of refrigerants is considered to be an irreversible process, leading to disposal of the mixed refrigerant as hazardous waste. U.S. Pat. No. 4,939,905, assigned to the assignee hereof, discloses a refrigerant recovery system that includes a recovery compressor, a multiple-section condenser, and means for automatically distinguishing between R12, R22 and R502 refrigerants at the compressor inlet, as a function of refrigerant vapor pressure and temperature, and switching the compressor outlet among the condenser sections to prevent mixing of refrigerants in the condenser. However, the temperature/saturation pressure characteristics of R12, R134a and blend refrigerants are such that these refrigerants cannot as readily be distinguished as a function of these characteristics.

There are currently available or will soon become available at least twenty-one different refrigerants that can be employed in various types of automotive and non-automotive refrigeration equipment. There is therefore a need in the refrigeration system service industry for a device that can be employed to test refrigerant in a storage container before using the refrigerant, or in a refrigeration system before performing service on the system, that is not restricted to any particular type of refrigerant or to automotive service applications, that is particularly well adapted to identify and distinguish between and among refrigerants of different types, that is inexpensive to manufacture and market, that is readily portable, that is rapid and efficient in operation, and/or that can be employed by relatively untrained service personnel.

U.S. Pat. No. 5,158,747 discloses such a device for identifying and distinguishing between and among different types of refrigerants. The device includes a fixed volume for containing a sample of refrigerant. The refrigerant to be tested is selectively admitted into the volume in vapor phase, vapor pressure of refrigerant within the fixed volume is measured, and admission of refrigerant into the fixed volume is terminated when the vapor pressure of refrigerant contained therein reaches a preselected level. A sensor and associated electronics are coupled to the sample-containing volume for determining type of refrigerant vapor as a function of one or more selected properties of the refrigerant, and indicating such refrigerant type to an operator.

U.S. application Ser. No. 08/047,263, filed Apr. 12, 1993 and assigned to the assignee hereof, discloses an improvement on the apparatus described in the patent noted immediately above in which a fixed volume contains a refrigerant sample at controlled pressure. A thermistor provides a first electrical signal as a function of the combined effect of thermoconductivity and temperature of the refrigerant sample in the sample-containing volume, and a temperature sensor provides a second electrical signal as a function of temperature of the refrigerant vapor in the sample-containing volume essentially independent of thermoconductivity thereof. Associated electronics determine type of refrigerant in the sample-containing volume as a function of the first and second electrical signals, and thus as a function of thermoconductivity of the refrigerant sample independent of sample temperature. Since thermoconductivity of refrigerants at a given temperature and pressure varies for different refrigerant types, refrigerant type can be determined and displayed to an operator.

A general object of the present invention is to provide a method and apparatus for identifying and distinguishing a wide variety of different refrigerant types that is economical to assemble, easy to use, and reliable over an extended useful life.

SUMMARY OF THE INVENTION

Refrigerant type is identified and determined in accordance with presently preferred embodiments of the invention by storing in electronic memory indicia representative of saturation pressure/temperature characteristics of a plurality of differing refrigerant types. A liquid refrigerant sample of unknown type is obtained and vaporized under controlled conditions of temperature and pressure. In accordance with one aspect of the invention, refrigerant vapor temperature is measured at two different vapor pressures during the vaporization process, and such temperatures and pressures are then compared with the indicia prestored in memory. Two temperature readings at differing vapor pressures are sufficient to distinguish refrigerant type based upon the prestored saturation/temperature indicia.

In accordance with another aspect of the invention, one of the vapor temperature readings is obtained at a vapor pressure equal to atmospheric pressure, which is defined as the boiling point of the refrigerant. This temperature reading alone is sufficient to distinguish almost all refrigerant types from each other. The boiling point temperature reading is obtained in accordance with preferred embodiments of the invention by obtaining a liquid refrigerant sample and then directing the liquid refrigerant sample, through an orifice to atmospheric pressure. The boiling point temperature reading is obtained at the outlet of the orifice. Most preferably, the vaporized refrigerant sample is collected in a holding container, rather than vented to atmosphere.

The liquid refrigerant sample may be obtained by drawing a refrigerant sample into a containment volume, and condensing the refrigerant sample in the containment volume if in vapor phase. The sample refrigerant may be drawn into the containment volume by evacuating the containment volume, and then connecting the containment volume to a refrigerant sample source such that the refrigerant sample is drawn into the containment volume by reduced pressure therewithin.

BRIEF DESCRIPTION OF THE DRAWINGS

The invention, together with additional objects, features and advantages thereof, will be best understood from the following description, the appended claims and the accompanying drawings, in which:

DETAILED DESCRIPTION OF PREFERRED EMBODIMENTS

Figure 1:
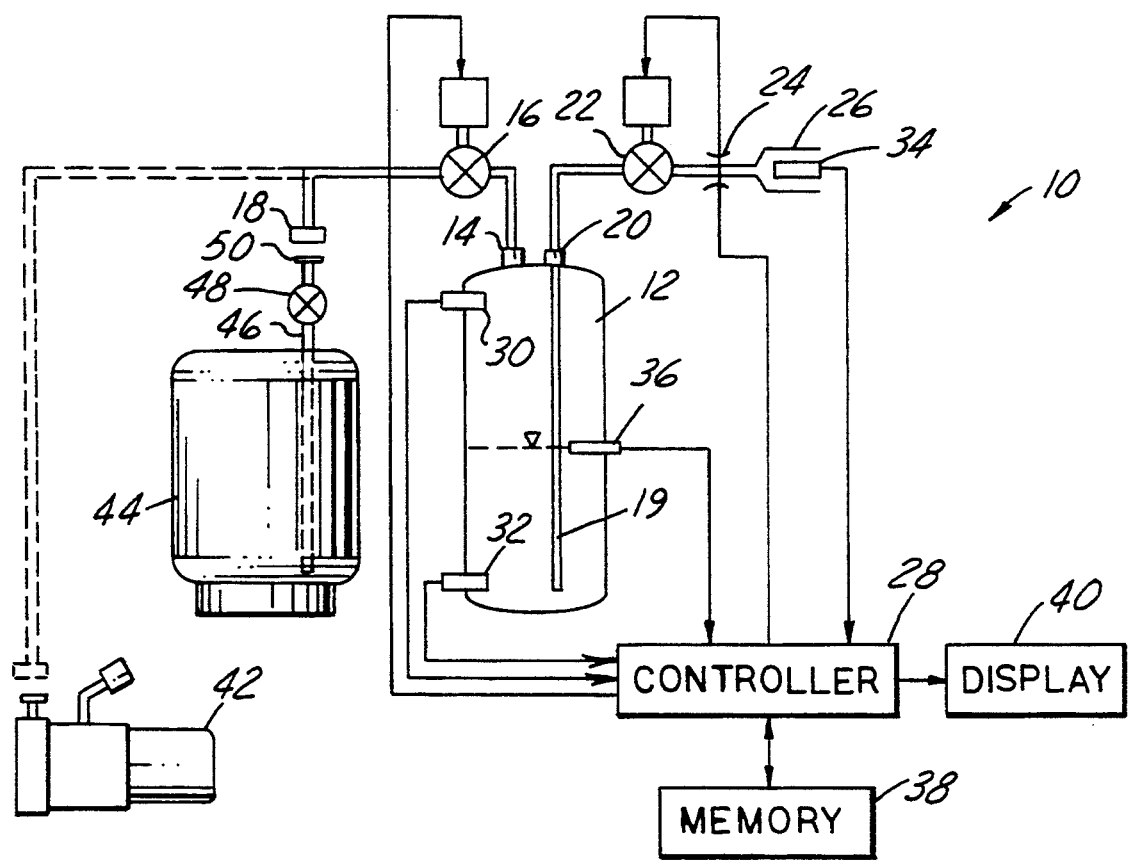
FIG. 1 is a schematic diagram of a refrigerant sampling and testing apparatus in accordance with a first embodiment of the invention.

FIG. 1 illustrates an apparatus 10 for identifying and distinguishing refrigerant types in accordance with one embodiment of the invention as comprising a liquid refrigerant sample containment vessel 12 having an inlet 14 connected through a solenoid valve 16 to a self-sealing quick-disconnect coupling 18. The outlet 20 of vessel 12 is connected through a second solenoid valve 22 and an orifice 24 to a purge vent 26. A pressure sensor 30 provides an electrical signal to a controller 28 indicative of refrigerant vapor pressure at the upper portion of sample containment vessel 12. A first temperature sensor 32 disposed at the lower portion of vessel 12 provides an electrical signal to controller 28 indicative of temperature of liquid refrigerant contained within the vessel. A second temperature sensor 34 is disposed at purge vent 28, and provides an electrical signal to controller 28 indicative of refrigerant vapor temperature that exits vent 26 at atmospheric pressure. Controller 28 also receives an electrical signal from a level sensor 36, which is responsive to a level of liquid refrigerant within vessel 12 above temperature sensor 32 but below pressure sensor 30. Controller 28 provides signals to control operation of solenoid valves 16,22. An electronic memory 38 contains prestored indicia in the form of a look-up table or the like, that relates saturation pressure to temperature for a plurality of refrigerants. Memory 38 is connected to controller 28, as is a display 40 for indicating refrigerant type to an operator.

Refrigerant vapor pressure versus temperature data is published by refrigerant manufacturers. The following table illustrates refrigerant vapor temperature at atmospheric pressure, defined as refrigerant boiling point, and refrigerant saturation pressure at 50° F., for twenty-one refrigerants currently available or soon to be available in quantity for use in various types of refrigeration equipment:

TABLE I

| Refrig. Type | Boiling Point (°F.) | Saturation Pressure at 50° F. (psig) |
| --- | --- | --- |
| R113 | 117.6 | −11.2 |
| R141b | 90.0 | −8.2 |
| R123 | 82.2 | −7.4 |
| R11 | 74.5 | −5.9 |
| R114 | 38.6 | 3.9 |
| R124 | 10.5 | 19.4 |
| R134a | −15.1 | 45.1 |
| R12 | −21.6 | 46.7 |
| MP39 | −26.2 | 56.1 |
| R500 | −28.3 | 57.5 |
| MP66 | −29.2 | 60.7 |
| R22 | −41.5 | 84.1 |
| R502 | −49.8 | 97.4 |
| AZ50 | −51.7 | 106.8 |
| HP81 | −53.0 | 106.7 |
| R125 | −55.4 | 117.1 |
| HP80 | −56.0 | 115.3 |
| AZ20 | −62.5 | 145.0 |
| R13 | −114.6 | 350.4 |
| R23 | −115.6 | 457.0 |
| R503 | −126.1 | 490.2 |

It will be noted from this Table that at least 2° F. separates the boiling points of the refrigerants with the exception of the following pairs: R500 and MP66, AZ50 and HP81, R125 and HP80, R502 and AZ50, and R13 and R23. Using the saturation pressure at 50° F., the R500/MP66 pair can be distinguished by the 3.2 psig pressure difference, the R502/AZ50 pair can be distinguished by a 9.4 psig pressure difference, and the R13/R23 pair can be distinguished by the 106.6 psig pressure difference.

In operation of apparatus 10 illustrated in FIG. 1, coupling 18 is first connected to a vacuum pump 42, and the vacuum pump is operated with solenoid valve 16 open and solenoid valve 22 closed to evacuate containment vessel 12 and the refrigerant conduits upstream of valve 22. (Orifice 24 and vent 26 are open to atmosphere.) With vessel 12 so evacuated, self-sealing coupling 18 is disconnected from vacuum pump 42, and is connected to a source of a liquid refrigerant sample of unknown type. In FIG. 1, the source is illustrated as a refrigerant storage container 44 having a liquid port 46 connected by a manual valve 48 to a fitting 50. It will be appreciated, however, that the source of the unknown liquid refrigerant sample could be any number of other devices, including the low pressure port of refrigeration equipment under service. In any event, liquid refrigerant is drawn from container 44 into vessel 12 through valve 16 up to the level of sensor 36, at which point valve 16 is closed by controller 28. Valve 22 is then opened, so that liquid refrigerant within vessel 12, drawn from the lower portion thereof by lift tube 19, is vented to atmosphere through orifice 24 and vent 26.

When the temperature at sensor 34 has stabilized, controller 28 obtains temperature readings from sensors 32,34 and a pressure reading from sensor 30. Sensor 30 indicates saturation pressure at the refrigerant temperature indicated by sensor 32, and sensor 34 indicates refrigerant vapor temperature at atmospheric pressure —i.e., refrigerant boiling point. With these two pressure/temperature readings, refrigerant type can be determined by comparing the data so obtained to the data prestored in memory 38, and refrigerant type indicated to an operator at display 40. As noted above in connection with Table I, refrigerant boiling point temperature alone is sufficient to identify most of the listed refrigerant types. For refrigerants having boiling point temperatures sufficiently close to each other within the measurement sensitivity of sensor 34—e.g., within 2° F.—the additional pressure and temperature data from sensors 30,32 is needed.

Figure 2:
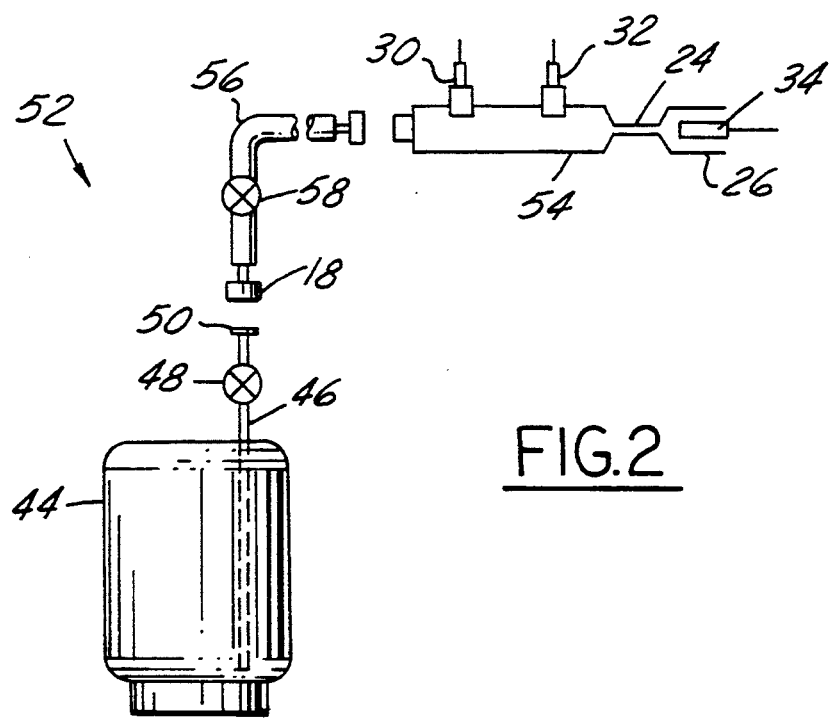
FIG. 2 is a schematic diagram of a refrigerant sampling and testing apparatus in accordance with a second embodiment of the invention.

FIG. 2 illustrates a modified embodiment 52 of the invention that is particularly useful for refrigerants that boil below ambient temperatures normally encountered in a refrigerant service environment—i.e., R114 and below in Table I. In apparatus 52, the liquid refrigerant sample containment volume is provided by a section of tubing 54 connectable by a hose 56 with coupling 18 to a source of a liquid refrigerant sample—e.g., refrigerant storage container 44. A manual valve 58 is positioned in hose 56, and tube section 54 is connected through orifice 24 to vent 26. Pressure sensor 30 and temperature sensor 32 are disposed in tube section 54, and temperature sensor 34 is disposed at vent 26 as in the embodiment of FIG. 1. When coupling 18 is connected to fitting 50 and valves 48,54 are opened, liquid refrigerant within container 44 is fed to tube section 54, and thence through orifice 24 to vent 26. Pressure sensor 30 and temperature sensor 32 are respectively connected to controller 28 (FIG. 1) to provide pressure and temperature measurements of the liquid refrigerant within tube section 54 as in the embodiment of FIG. 1, and temperature sensor 34 measures refrigerant boiling point temperature as in the embodiment of FIG. 1. The embodiment of FIG. 2 is more economical than the embodiment of FIG. 1, and provides more accurate temperature and pressure readings at sensors 32,30 since there would be no temperature gradients within tube-section containment vessel 54.

Figure 3:
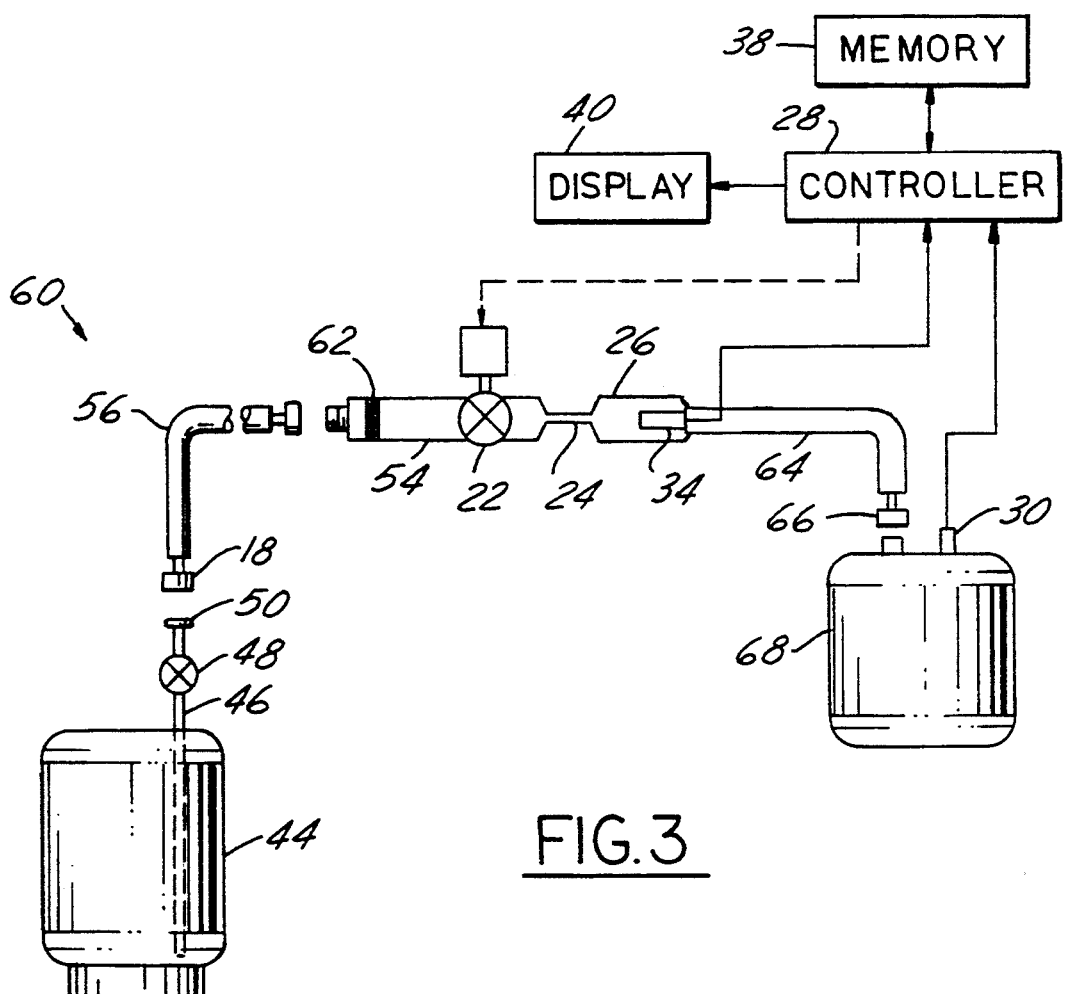
FIG. 3 is a schematic diagram of a refrigerant sampling and testing apparatus in accordance with a third embodiment of the invention.

FIG. 3 illustrates an apparatus 60 in accordance with another embodiment of the invention. Tube-section sample containment vessel 54 is connectable by hose 56 as in FIG. 2, and has an inlet screen 62 for preventing entry of particular materials. Temperature sensor 32 and pressure sensor 30 are not positioned in tube section 54 as in the embodiment of FIG. 2, and a solenoid valve 22 is positioned between tube section 54 and orifice 24. Vent 26 is connected by a hose 64 and a coupling 66 to a sample holding vessel 68. Pressure sensor 30 is coupled to vessel 68, and provides a signal to controller 28 indicative of refrigerant vapor pressure within vessel 68. In use of apparatus 60 in FIG. 3, hose 56 is connected to tube section 54 and hose 64 is connected to holding vessel 68. Coupling 18 is then connected to vacuum pump 42 (FIG. 1), and valve 52 is opened by controller 28 to evacuate the apparatus including vessel 68. Coupling 18 is then connected to fitting 50 of storage vessel 44, and valve 22 remains open so that liquid refrigerant is drawn through containment section 54, orifice 24 and hose 64 to vessel 68. Controller 28 samples the outputs of pressure sensor 30 and temperature sensor 34 at a first low pressure level such as at twenty inches of mercury, and again samples the output of temperature sensor 34 when pressure sensor indicates atmospheric pressure within vessel 68. If these readings indicate that the refrigerant sample has a relatively high boiling temperature, these readings are sufficient to determine refrigerant type, and valve 22 is closed to prevent excess pressure within vessel 68. However, if the first two temperature readings indicate a refrigerant having low boiling point, valve 22 remains open and a third pressure/temperature reading is obtained at higher pressure within vessel 68. This technique prevents venting of refrigerant into the atmosphere by capturing the refrigerant within containment vessel 68, while at the same time preventing overfilling and condensation within the container.

Figure 4:
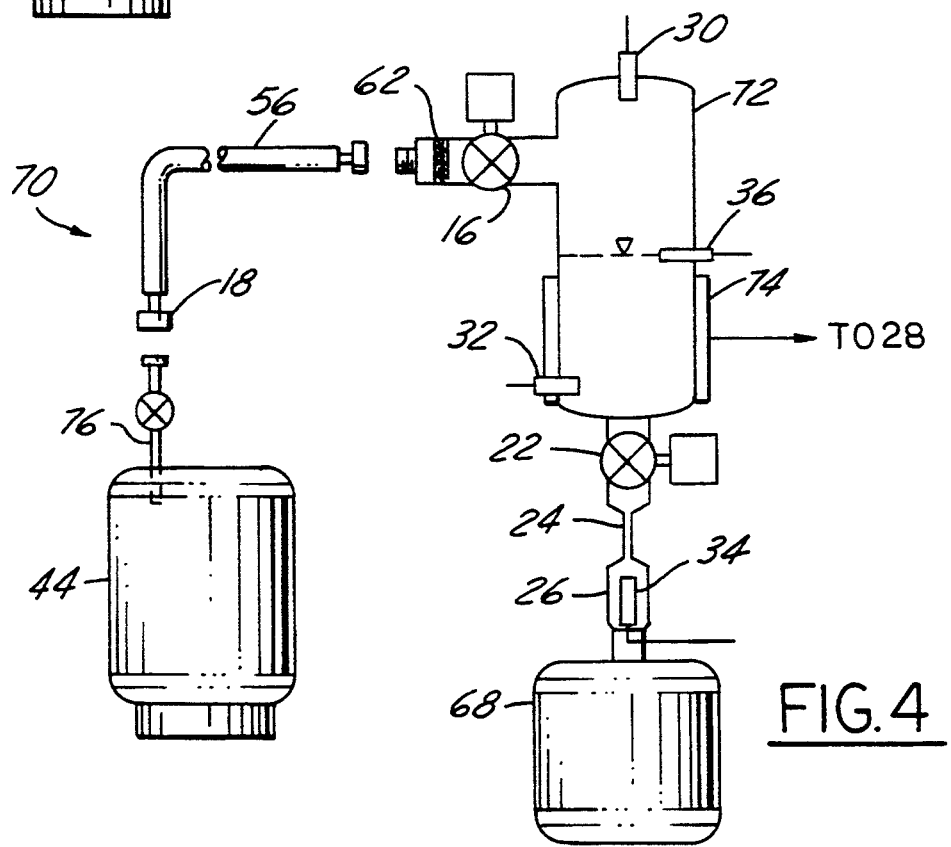
FIG. 4 is a schematic diagram of a refrigerant sampling and testing apparatus in accordance with a fourth embodiment of the invention.

FIG. 4 illustrates an apparatus 70 that is a modification to apparatus 10 in FIG. 1 and apparatus 60 in FIG. 3. The sample containment vessel 72 in FIG. 4 receives a refrigerant sample through solenoid valve 16 and hose 56, and vaporizes refrigerant through solenoid valve 22 and orifice 24 into sample holding vessel 68. Level sensor 30 prevents overfilling of vessel 72. A thermoelectric sleeve 74 is disposed in heat conductive communication with vessel 72 outside of the vessel, and is connected to controller 28 (FIGS. 1 and 3) for selectively either heating or cooling refrigerant within vessel 72. Thermoelectric device 74 allows inlet fitting 18 to be connected to the vapor port 76 of storage vessel 44 for drawing refrigerant vapor into sample containment vessel 72, which sample can then be liquified by cooling the containment vessel. Alternatively, thermoelectric device 74 may be used to heat vessel 72 until pressure sensor 30 indicates a vapor pressure of one atmosphere, at which point temperature sensor 32 will indicate boiling point temperature as hereinabove described.

Figure 5:
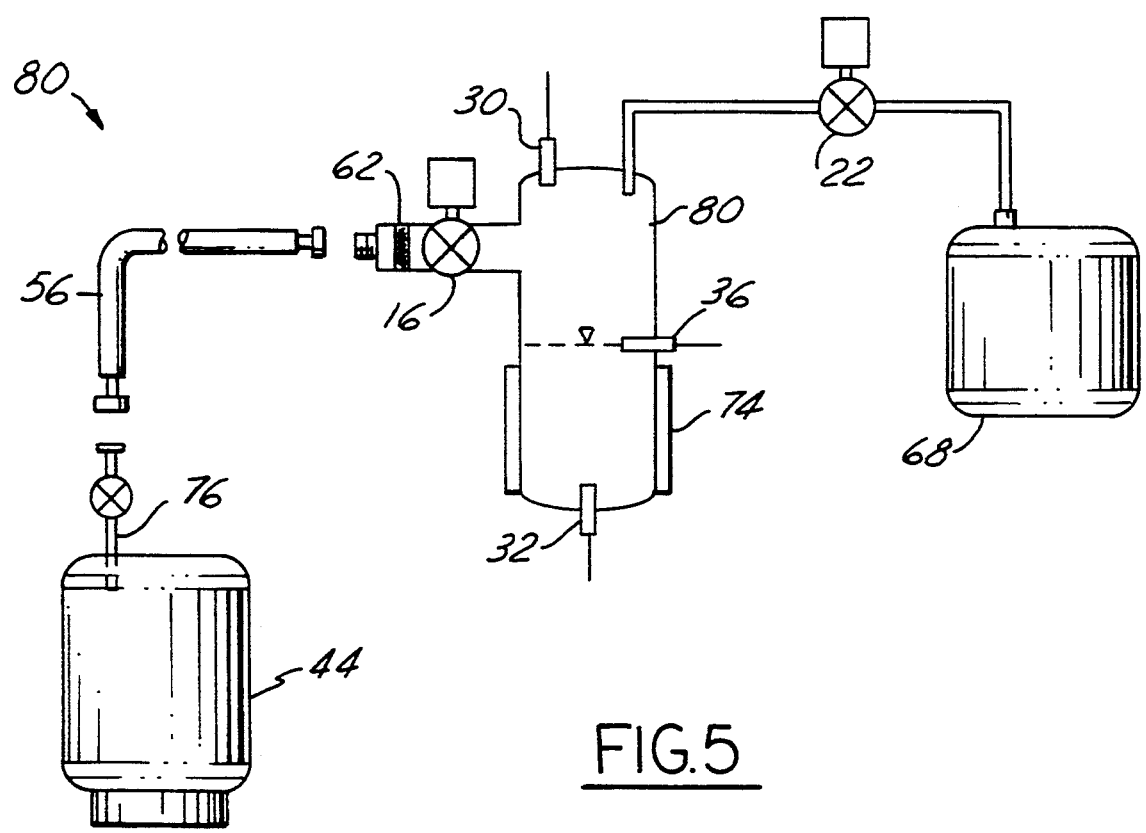
FIG. 5 is a schematic diagram of a refrigerant sampling and testing apparatus in accordance with a fifth embodiment of the invention.

Another modified embodiment 80 of the present invention is illustrated in FIG. 5. In this embodiment, the thermoelectric condenser/heater 74 is wrapped around a sample containment vessel 82 which has a vapor outlet connected through valve 22 to holding vessel 68. In this embodiment, there is no orifice 24 or purge vent 26 with temperature sensor for measuring boiling point. Rather, pressure sensor 30 and temperature sensor 32 are connected to controller 28 (FIG. 1), which samples the output of temperature sensor 32 when pressure sensor 30 indicates atmospheric pressure within vessel 12. Once again, temperature readings at selected pressure levels above and below atmospheric pressure may be obtained as in the embodiment of FIG. 3.

I claim:

1. A method of determining refrigerant type comprising the steps of:
    (a) storing in electronic memory indicia representative of saturation pressure/temperature characteristics of a plurality of differing refrigerant types,
    (b) obtaining a liquid refrigerant sample of unknown type,
    (c) vaporizing the liquid refrigerant sample under controlled conditions of temperature and pressure, (d) measuring refrigerant temperature at two different vapor pressures during said step (c), (e) comparing said temperatures measured in said step (d) to said stored indicia, and (f) determining type of refrigerant in said liquid sample as a function of said comparison in said step (e).

2. The method set forth in claim 1 wherein said step (d) includes the step of measuring said refrigerant temperature at a refrigerant vapor pressure equal to atmospheric pressure.

3. The method set forth in claim 1 wherein said step (c) comprises the step of directing the liquid refrigerant sample through an orifice.

4. The method set forth in claim 1 wherein said step (b) comprises the step of drawing a liquid refrigerant sample into a containment volume.

5. The method set forth in claim 1 wherein said step (b) comprises the steps of: (b1) drawing a refrigerant sample into a containment volume in vapor phase, and (b2) condensing the refrigerant sample in the said containment volume.

6. The method set forth in claim 1 wherein said step (b) comprises the steps of: (b1) evacuating a containment volume, and then (b2) connecting said containment volume to a refrigerant sample source such that the refrigerant sample is drawn into said containment volume by reduced pressure therein.

7. The method set forth in claim 1 comprising the additional step of: (g) capturing refrigerant vapor generated in said step (c).

8. A method of determining refrigerant type comprising the steps of:
(a) obtaining a liquid refrigerant sample of unknown type,
(b) vaporizing the liquid refrigerant sample,
(c) measuring temperature of refrigerant vapor generated in said step (b) at atmospheric pressure, and
(d) determining refrigerant type as a function of refrigerant vapor temperature measured in said step (c).

9. The method set forth in claim 8 Wherein said step (b) comprises the step of directing the liquid refrigerant sample through an orifice to atmospheric pressure.

10. The method set forth in claim 9 wherein said step (c) comprises the step of measuring the temperature of refrigerant vapor exiting said orifice.

11. The method set forth in claim 10 comprising the additional step of: (e) capturing refrigerant vapor exiting said orifice.

12. The method set forth in claim 8 wherein said step (d) comprises the step of displaying said refrigerant vapor temperature measured in said step (c).

13. The method set forth in claim 8 comprising the additional step, prior to said step (a), of: (e) storing in electronic memory indicia indicative of vapor temperature at atmospheric pressure for a plurality of differing refrigerants, and wherein said step (d) comprises the steps of: (d1) comparing said refrigerant vapor temperature measured in said step (c) with said indicia stored in said step (e), and (d2) determining refrigerant type as a function of said comparison in said step (d1).

14. The method set forth in claim 8 wherein said step (a) comprises the step of drawing a liquid refrigerant sample into a containment volume.

15. The method set forth in claim 8 wherein said step (a) comprises the steps of: (a1) drawing a refrigerant sample into a containment volume in vapor phase, and (a2) condensing the refrigerant sample in the said containment volume.

16. The method set forth in claim 8 wherein said step (a) comprises the steps of (a1) evacuating a containment volume, and then (a2) connecting said containment volume to a refrigerant sample source such that the refrigerant sample is drawn into said containment volume by reduced pressure therein.

17. Apparatus for identifying refrigerant type comprising:
means for obtaining a refrigerant sample in liquid phase,
means for vaporizing the liquid refrigerant sample by directing the sample through an orifice to atmospheric pressure,
temperature sensing means for providing an electrical signal as a function of temperature of refrigerant vapor exiting said orifice to atmospheric pressure, and
means for determining refrigerant type as a function of said electrical signal.

18. The apparatus set forth in claim 17 wherein said means for obtaining the refrigerant sample comprises a containment volume, means for evacuating said containment volume, and means for connecting the evacuated containment volume to a source of unknown refrigerant.

19. The apparatus set forth in claim 17 wherein said means for obtaining the refrigerant sample comprises a containment volume, means for connecting said containment volume to a source of unknown refrigerant type in either liquid or phase, and means for condensing a vapor phase refrigerant sample within said containment volume.

20. Apparatus for identifying refrigerant type comprising:
an electronic memory having prestored therein indicia that relates refrigerant saturation pressure to temperature for a plurality of differing refrigerants,
means for obtaining a liquid refrigerant sample,
means for vaporizing said liquid refrigerant sample at atmospheric pressure,
means for measuring refrigerant vapor temperature during operation of said vaporizing means at two differing refrigerant vapor pressures, one of which is atmospheric pressure,
means for comparing such refrigerant vapor temperatures and pressures to said indicia stored in memory, and
means for determining refrigerant type as a function of such comparison.

21. The apparatus set forth in claim 20 further comprising means for capturing the vaporized liquid refrigerant sample.

22. Apparatus for identifying refrigerant type comprising:
an electronic memory having prestored therein indicia that relates refrigerant saturation pressure to temperature for a plurality of differing refrigerants,
means for obtaining a liquid refrigerant sample,
means for vaporizing said liquid refrigerant sample,
means for measuring refrigerant vapor temperature at two differing refrigerant vapor pressures during operation of said vaporizing means,
means for comparing such refrigerant vapor temperatures and pressures to said indicia stored in memory, means for determining refrigerant type as a function of such comparison, and means for capturing the vaporized liquid refrigerant sample.

23. The apparatus set forth in claim 22 wherein said vaporizing means comprises means for vaporizing said liquid refrigerant sample at atmospheric pressure, and means for measuring refrigerant vapor temperature at atmospheric pressure as one of said two differing vapor pressures.

* * * * *